(12) United States Patent
Zinnen et al.

(10) Patent No.: US 6,410,794 B1
(45) Date of Patent: Jun. 25, 2002

(54) PROCESS FOR PREPARATION OF PHARMACEUTICALLY DESIRED CHIRAL TETRALONE FROM TETRALONES

(75) Inventors: Herman A. Zinnen, Evanston; Mark J. Gattuso, Palatine, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/705,306

(22) Filed: Nov. 3, 2000

(Under 37 CFR 1.47)

Related U.S. Application Data

(63) Continuation-in-part of application No. 09/255,300, filed on Feb. 22, 1999, now Pat. No. 6,162,949, which is a continuation-in-part of application No. 08/357,910, filed on Dec. 16, 1994, now Pat. No. 5,889,186.

(51) Int. Cl.⁷ .............................................. C07C 63/00
(52) U.S. Cl. ...................... 568/309; 558/415; 568/319; 568/322; 568/327
(58) Field of Search .................... 558/415; 568/309, 568/319, 322, 237

(56) References Cited

U.S. PATENT DOCUMENTS

| | | | |
|---|---|---|---|
| 2,985,589 A | 5/1961 | Broughton et al. | 210/34 |
| 4,536,518 A | 8/1985 | Welch, Jr. et al. | 514/647 |
| 4,556,676 A | 12/1985 | Welch, Jr. et al. | 514/554 |
| 4,777,288 A | 10/1988 | Quallich et al. | 562/491 |
| 4,839,104 A | 6/1989 | Quallich et al. | 200/396 |
| 5,104,899 A | 4/1992 | Young et al. | 514/646 |
| 5,750,794 A | 5/1998 | Quallich | 568/322 |
| 5,889,186 A | 3/1999 | Gattuso | 564/304 |

FOREIGN PATENT DOCUMENTS

| | | |
|---|---|---|
| WO | WO 99-57089 | 11/1999 |

OTHER PUBLICATIONS

Skrebnik, Ramachandran & Brown, *J. Org. Chem.* 53, 2916, 1988.
Gao & Sharpless, *J. Org. Chem.* 53, 4081, 1988.
E.J. Corey and G.A. Reichard, *Tetrahedron Letters*, 30, No. 39, 5207 (1989).
Schneider and Goergens, *Tetrahedron: Asymmetry*, No. 4, 525, 1992.
W.M. Whitesides, et al. *Journal of the American Chemical Society*, vol. 91, No. 17, p. 4871 (1989).
K. Mori et al., *Synthesis*, p. 752 (1982).
B.H. Lipshutz et al., *Journal of Organic Chemistry*, vol. 49, p. 3928 (1984).
Quallich, G.J. and Woodall, T.M., *Tetrahedron*, vol. 48, No. 47, p. 10239 (1992).

*Primary Examiner*—Richard L Raymond
(74) *Attorney, Agent, or Firm*—John G. Tolomei; Frank S. Molinaro; Maryann Maas

(57) ABSTRACT

Improved processes for preparation of tetralones in high enantiomeric purity centers on resolution using simulated moving bed chromatography of a racemic tetralone derivative. Resolution is effected with high enantiomeric purity, and subsequent reactions of the desired tetralone derivative enantiomer performed with high optical specificity to maintain enantiomeric purity. The undesired enantiomer may be racemized and recycled to the resolution phase to avoid loss.

23 Claims, 3 Drawing Sheets

PROCESS FOR PREPARATION OF PHARMACEUTICALLY DESIRED CHIRAL TETRALONE FROM TETRALONES

CROSS REFERENCE TO RELATED APPLICATIONS

This application is a continuation-in-part of our copending application, application Ser. No. 09/255,300, filed Feb. 22, 1999, which in turn is a continuation-in-part of application Ser. No. 08/357,910 filed Dec. 16, 1994, now U.S. Pat. No. 5,889,186 all of which are hereby incorporated by reference.

BACKGROUND OF THE INVENTION

At the molecular level biological systems are highly asymmetric; enzymes, proteins, polysaccharides, nucleic acids, and many other fundamental components of life are present in optically active form. The implications of this are profound; as a general proposition the interaction of a chiral molecule with an optically active site is a diastereomeric interaction, and the two enantiomers properly should be viewed as distinct compounds capable of acting in different ways. (R)-Asparagine has a bitter taste, whereas the (S)-isomer is sweet. It has been known for some time that for medicinals having at least one chiral center the pharmacological effectiveness of the enantiomers of the racemic mixture may differ substantially, and in some cases the pharmacological action itself may differ. An extreme example is provided by propranolol, where the major pharmacological effect of the (R)-isomer is as a contraceptive, whereas the major pharmacological effect of the (S)-isomer is as a beta-blocker.

Although the recognition of the desirability of using the pharmacologically and pharmaceutically more acceptable enantiomer is old, nonetheless the use of optically pure medicinals generally is relatively new, simply because of the difficulty and cost of resolution of the racemic mixture and/or the difficulty and cost of asymmetric synthesis of the desired enantiomer. The importance of stereochemical purity may be exemplified by (S)-propranolol, which is known to be 100 times more potent as a beta-blocker than its (R)-enantiomer. Furthermore, optical purity is important since certain isomers actually may be deleterious rather than simply inert. For example, the R-enantiomer of thalidomide was a safe and effective sedative when prescribed for the control of morning sickness during pregnancy. However, S-thalidomide was discovered to be a potent teratogen leaving in its wake a multitude of infants deformed at birth.

With recent chemical advances, especially in asymmetric synthesis, has come both an increase in the feasibility of selectively preparing the desired enantiomer of a given chiral medicinal, as well as increasing pressure on the pharmaceutical industry to make available only that enantiomer. An instructive example, pertinent to the subject matter of this invention, is the class of compounds having Formula I. An important member of this class is the antidepressant sertraline (available as Zoloft™), which has Formula II:

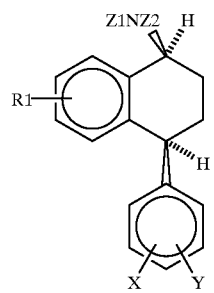

I

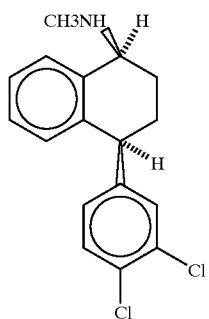

II

Useful precursors to compounds of Formula I are represented by tetralones having Formula III which are generally referred to as "tetralones" or where racemic, "racemic tetralones". A valuable synthetic precursor to sertraline is a tetralone, specifically, one enantiomer of the compound 4-(3,4-dichlorophenyl-3,4-dihydro-1(2H)-naphthalenone and, more specifically, (4S)-(3,4-dichlorophenyl-3,4-dihydro-1(2H)-naphthalenone with the structure IV:

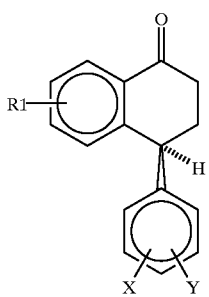

III

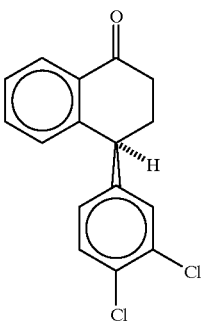

IV

Thus, G. J. Quallich and T. M. Woodall, *Tetrahedron*, Vol. 48, No.47, p. 10239, (1992) used SN2 cuprate displacement of an activated chiral benzylic alcohol, followed by intramolecular Friedel-Crafts acylation of a diaryl carboxylic acid to yield the chiral tetralone of structure IV. Other documents relate to the synthesis of sertraline and to chiral tetralone, including U.S. Pat. No. 5,750,794; U.S. Pat. No. 4,536,518; U.S. Pat. No. 4,556,676; U.S. Pat. No. 4,777,288; and U.S. Pat. No. 4,839,104. Other asymmetric methods of synthesis have been employed by those skilled in the art, such as those described by W. M. Whitesides, et. al, *Journal of the American Chemical Society*, Vol. 91, No. 17, p. 4871 (1969); K. Mori et. al., *Synthesis*, p. 752 (1982); and B. H. Lipshutz et. al., *Journal of Organic Chemistry*, Vol. 49, p. 3928, (1984).

The foregoing are examples of enantioselective synthesis relevant to the chiral tetralone precursor (structure IV) to sertraline. Enantioselective synthesis depends on chiral reagents of high enantiomeric purity which often are quite expensive. Consequently, another general approach is based on the efficient resolution of a precursor early in the synthesis of a chiral material. Resolution is effected with high enantiomeric purity and is followed by subsequent conventional synthetic techniques which maintain high enantiomeric purity in intermediates through final product formation. This approach is exemplified by the work of Schneider and Goergens, *Tetrahedron: Asymmetry*, No. 4, 525, 1992. These authors effected enzymatic resolution of 3-chloro-1-phenyl-1-propanol (CPP) via enzymatic hydrolysis of the racemic acetate in the presence of a lipase from *Pseudornonas fluorescens* under close pH control with a phosphate buffer. The hydrolysis was halted after about 50% conversion to afford the R-alcohol while leaving unchanged the S-acetate, which subsequently could be hydrolyzed with base to the S-alcohol. From the enantiomerically pure alcohols the enantiomerically pure serotonin-uptake inhibitors fluoxetine (whose racemate is available as Prozac™), tomoxetine, and nisoxetine could be prepared.

The Schneider and Goergens approach highlights a characteristic of methods based on resolution of a racemate which requires our attention. The authors used both the R- and S-CPP to prepare both R- and S-fluoxetine in high optical purity, although one enantiomer is substantially more desirable than the other (see U.S. Pat. No. 5,104,899, supra). Consequently, in practice only the more desirable enantiomer will be utilized in subsequent synthesis. There then results the economic burden of discarding the less desirable (or even undesirable) enantiomer—which is half of the raw material or (even worse) an intermediate in the synthesis of the desired enantiomer. Thus, it is imperative to somehow utilize the undesired enantiomer. Stated concisely, incident to a method of preparing medicinals of high optical purity based on using a raw material or intermediate of high enantiomeric purity obtained via resolution of its racemate is the requirement of utilizing the unwanted enantiomer produced as a by product in the resolution stage. Perhaps the most desirable utilization of the unwanted enantiomer would be to racemize it and recycle the racemate to the appropriate stage in the synthetic scheme; this application is directed precisely to such a process flow.

SUMMARY OF THE INVENTION

The purpose of the present invention is to present a process for the preparation of the more desirable enantiomer of tetralones. The invention comprises resolution of racemic tetralones by simulated moving bed chromatography using a chiral adsorbent to afford at least one substantially pure enantiomer of tetralones, utilization of the substantially pure tetralone enantiomer in the synthesis of sertraline or sertraline analogs, racemization of the enantiomer not further used in synthesis, with recycle thereof to the resolution stage. In a specific embodiment (4S)-(3,4-dichlorophenyl-3,4-dihydro-1(2H)-naphthalenone is utilized as the substantially pure enantiomer.

Another embodiment comprises the reduction of tetralones to the corresponding racemic alcohols, conversion of the racemic alcohols to the corresponding racemic hydroxyl-protected alcohols, resolution of racemic hydroxyl-protected alcohols by simulated moving bed chromatography using a chiral adsorbent to afford at least one substantially pure enantiomer of the hydroxyl-protected alcohols, de-protection of a selected hydroxyl-protected alcohol enantiomer to the corresponding alcohol, oxidation of said alcohol to the corresponding tetralone enantiomer, utilization of the substantially pure tetralone enantiomer in the synthesis of sertraline or sertraline analogs, and racemization of the other hydroxyl-protected alcohol enantiomer with its recycle to the resolution stage.

Yet another embodiment comprises the conversion of tetralones to the corresponding carbonyl-protected tetralones, resolution of carbonyl-protected tetralones by simulated moving bed chromatography using a chiral adsorbent to afford at least one substantially pure enantiomer of the carbonyl-protected tetralones, de-protection of a selected carbonyl-protected tetralone enantiomer to the corresponding tetralone or analog enantiomer, utilization of the substantially pure tetralone or analog enantiomer in the synthesis of sertraline or sertraline analogs, and racemization of the other selected carbonyl-protected tetralone enantiomer with its recycle to the resolution stage.

DESCRIPTION OF THE FIGURES

FIGS. 2–4 represent process flows for the preparation of chiral tetralones utilizing simulated moving bed chromatography to resolve racemic derivatives of tetralones into enantiomeric derivatives, conversion of tetralone derivative enantiomers into tetralones useful in sertraline or sertraline analog synthetic preparative routes, and recycle of the remaining tetralone derivative enantiomers to the separation stage.

DESCRIPTION OF THE INVENTION

The present invention is better understood in the context of synthetic routes to sertraline and sertraline analogs which can be derived from tetralones having the formula III

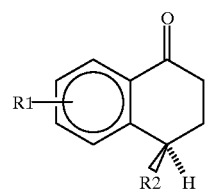

where R1 is selected from the group consisting of hydrogen, fluoro, chloro, bromo, trifluoromethyl, and alkoxy having from 1 to 3 carbon atoms, R2 has the structure

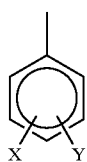

where X and Y are independently selected from the group consisting of hydrogen, fluoro, chloro, bromo, trifluoromethyl, and alkoxy having from 1 to 3 carbons and cyano, with at least one of X or Y being other than hydrogen. In a preferred embodiment, R1 is hydrogen, X is Cl, and Y is Cl.

The specific features of one generalized preparative route to sertraline and sertraline analogs, depicting only those features of central interest here, are given in equation (1):

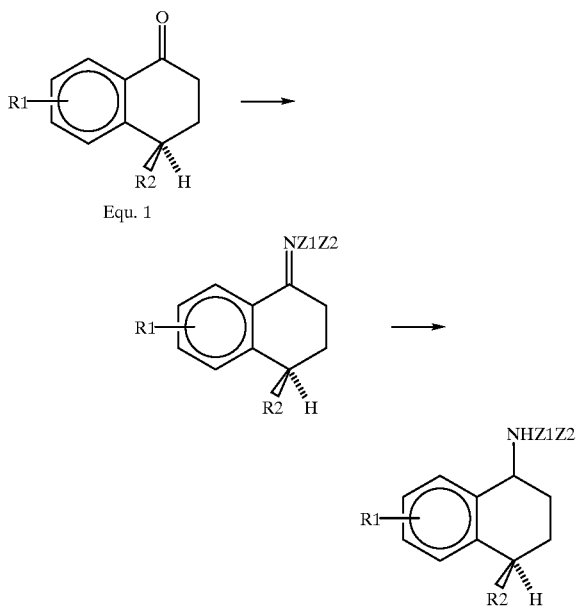

Equ. 1

The conversion shown in Equation 1 whereby tetralones are transformed to the corresponding immines, followed by reduction thereof to cis-(4S)-N-substituted-(disubstituted phenyl)-1,2,3,4-tetrhydro-1-naphthaleneamines (hereinafter, "racemic sertraline", or "racemic sertraline analogs"), can be accomplished by methods known in the art. In the case of sertraline and racemic sertraline, Z1 is hydrogen and Z2 is methyl. It is readily seen in this enantioselective synthesis of racemic sertraline or racemic sertraline analogs that a key element is the presence of the proper chirality at the carbon to which group R2 is attached. Thus, this synthesis involves yet further preparation of chiral precursors to tetralones, such synthesis generating and maintaining the specific desired chirality shown. In general, the time required and the expense of the chiral reagents consumed with such enantioselective synthesis can be considerable.

Figure 1:
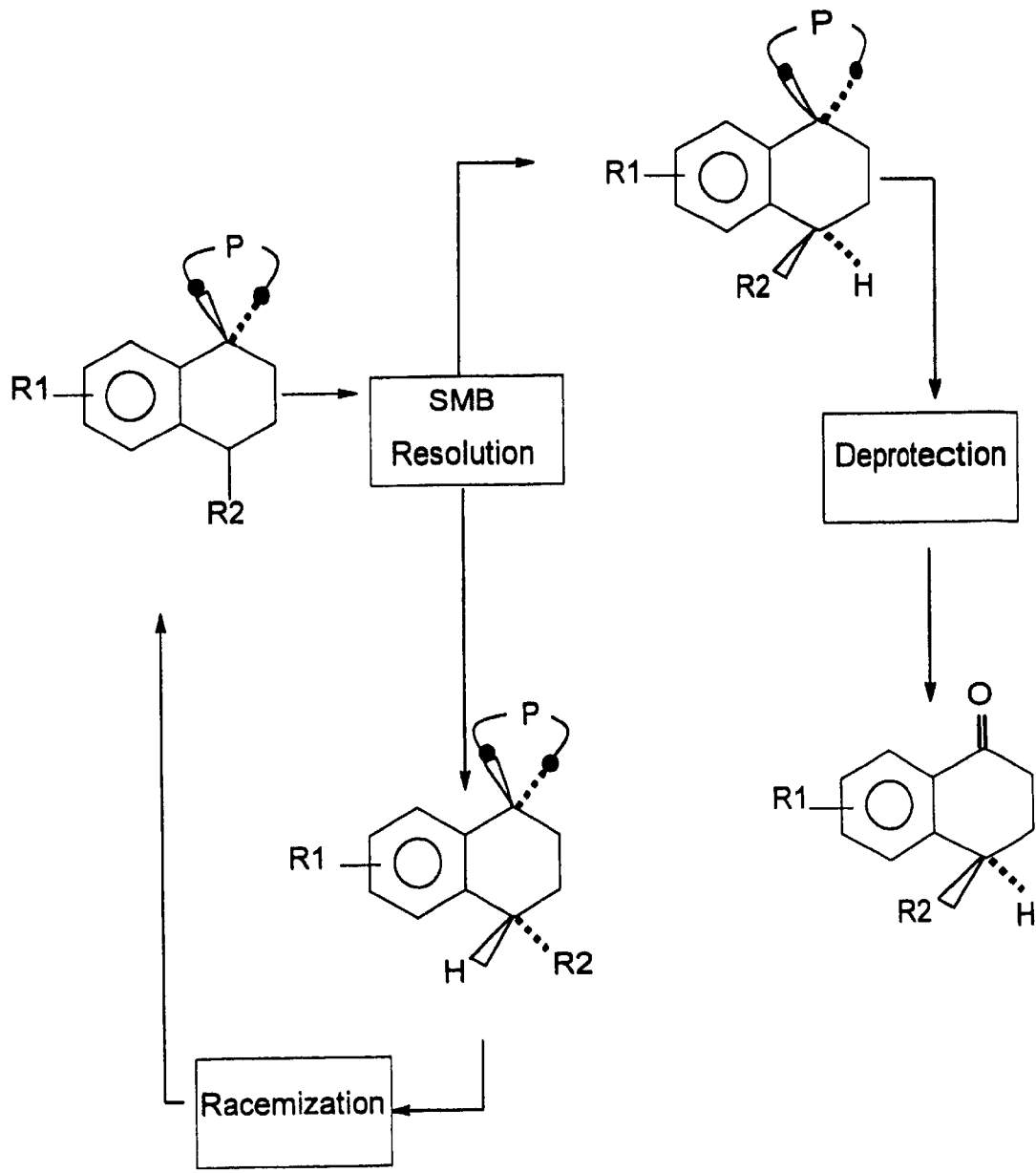
FIG. 1 represents a process flow for the preparation of chiral tetralones utilizing simulated moving bed chromatography to resolve racemic tetralones into enantiomers of tetralones, use of an enantiomer in sertraline or sertraline analog synthetic preparative routes, and recycle of the other tetralone enantiomer to the separation stage.
Figure 2:
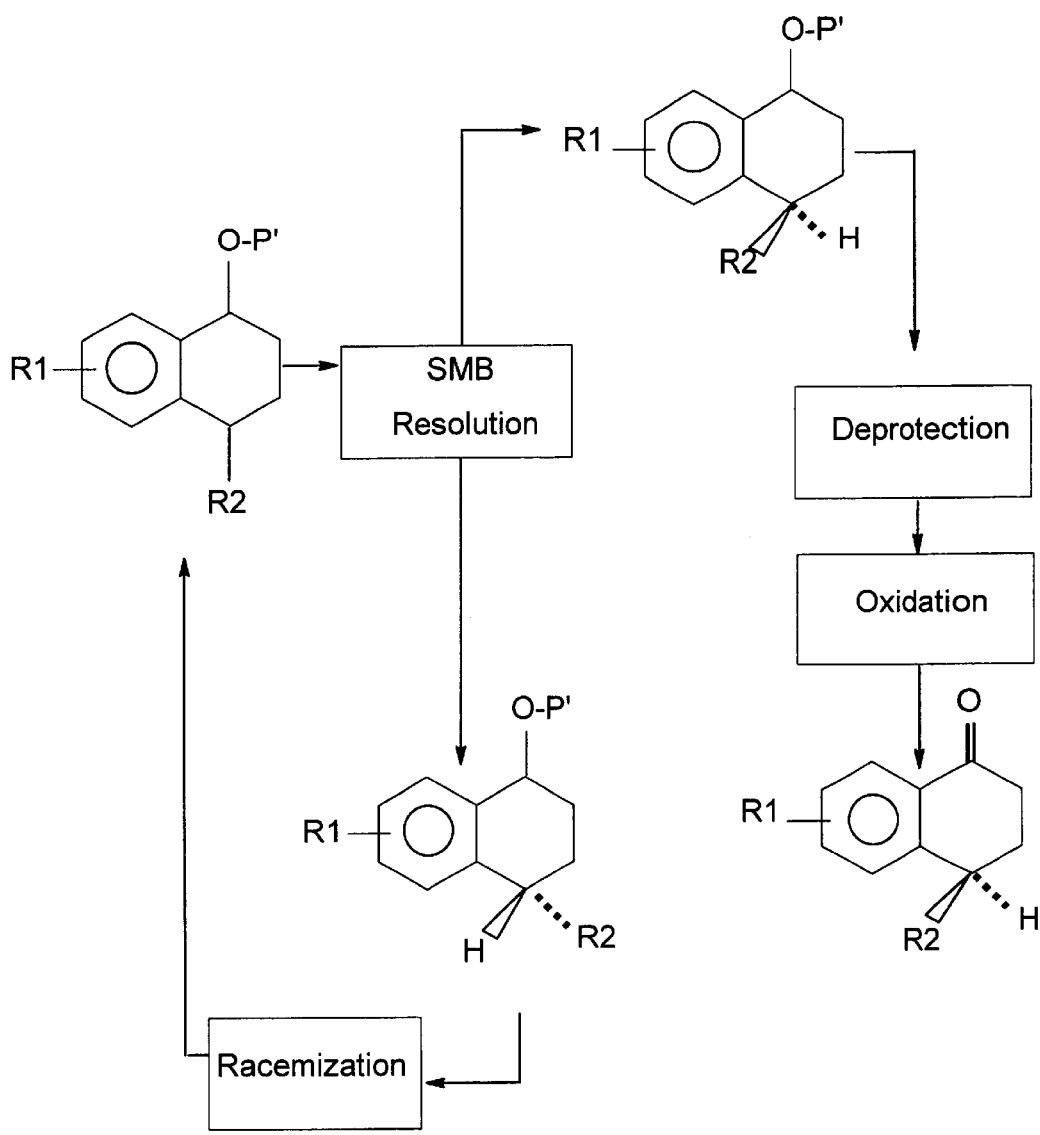
Figure 3:
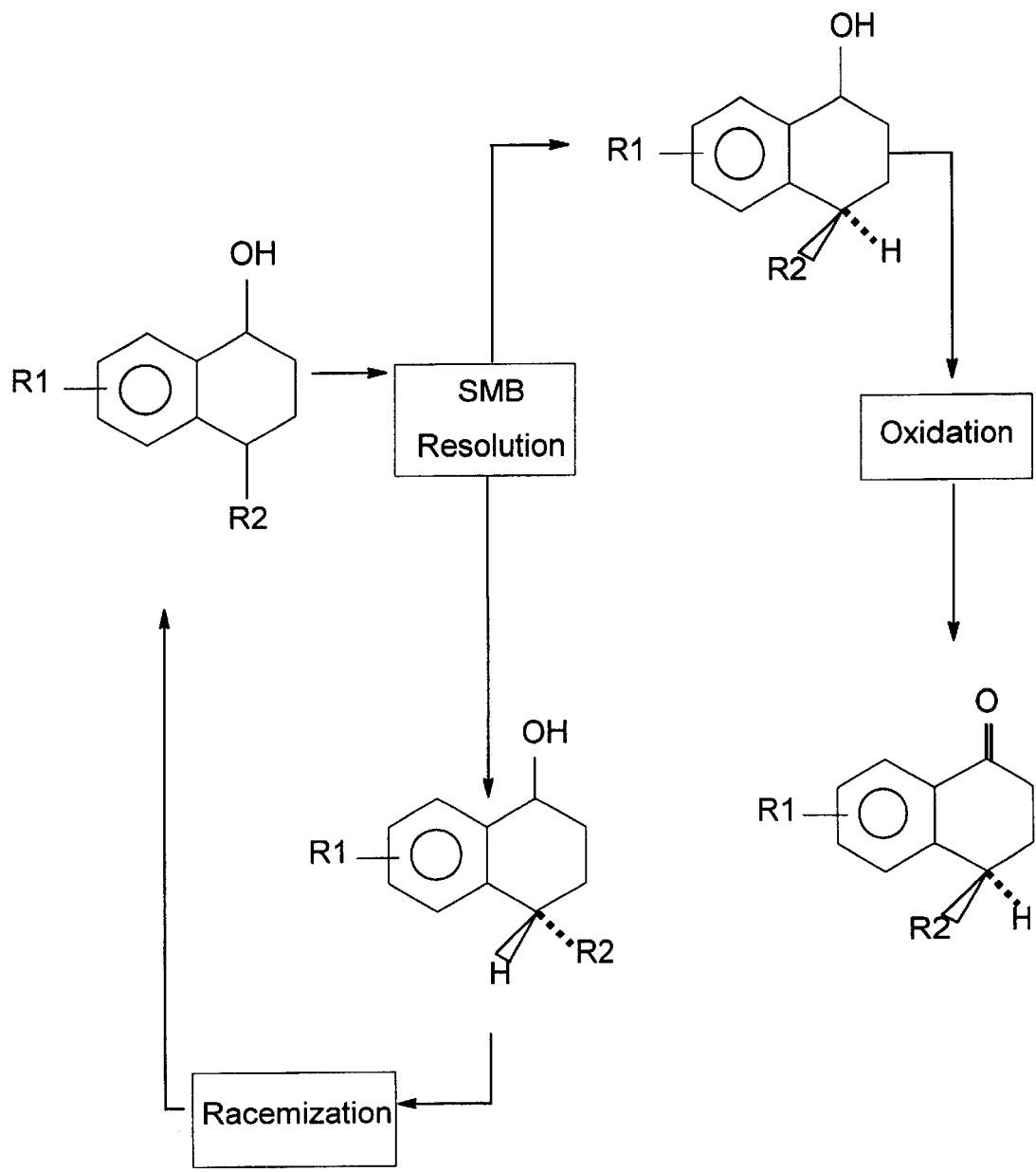

An advantage of our invention for preparing tetralones is that racemic derivatives, the synthesis of which can proceed without the need for expensive chiral reagents, may be resolved and the resulting desired enantiomeric derivatives of tetralones may then be converted to tetralones and used in the sertraline or sertraline analog synthesis, as illustrated in FIGS. 1–3. In FIG. 1 the derivatives are racemic tetralones, in which the carbonyl group is protected with a suitable protecting group P, as is known in the art. The protected racemic tetralones are then separated with the use of simulated moving bed chromatography using a chiral adsorbent to afford a substantially pure protected enantiomer of tetralones subsequently de-protected to afford tetralones, with racemization of the undesired protected enantiomer of tetralones and subsequent recycle to the resolution stage. In FIG. 2 the derivatives of racemic tetralones are the racemic alcohols, in which the hydroxyl group is protected with a suitable protecting group P', as is known in the art. The protected racemic alcohols are then separated with the use of simulated moving bed chromatography using a chiral adsorbent to afford a substantially pure protected alcohol enantiomer which is then de-protected, and oxidized to tetralones, with racemization of the undesired protected alcohol enantiomer and its subsequent recycle to the resolution stage. In FIG. 3 the derivatives of racemic tetralones are the corresponding racemic alcohols. The racemic alcohols are then separated with the use of simulated moving bed chromatography using a chiral adsorbent to afford a substantially pure alcohol enantiomer which is then oxidized to tetralones, with racemization of the undesired alcohol enantiomer and its subsequent recycle to the resolution stage. Since simulated moving bed chromatography is a continuous process, quality control can be more effective and can be continuous in the context that separation parameters may be changed incrementally at frequent intervals.

Before describing the specifics of the processes in FIGS. 1–3 we will briefly review simulated moving bed chromatography. The advantages of the moving bed of adsorbent in a countercurrent separation process have long been recognized. Because of the difficulty of an actual moving adsorbent bed, a flow scheme has been devised which maintains the process features of continuous countercurrent flow of fluid and solid without the actual movement of solids—i.e., a simulated moving bed.

In simulated moving bed processes the adsorption and desorption operations are continuously occurring which allow both continuous production of an extract and a raffinate stream with the continual use of feed and desorbent streams. A preferred embodiment of this process utilizes what is known in the art as the simulated moving bed countercurrent flow system. The operating principals and sequence of such a flow system are described in U.S. Pat. No. 2,985,589.

Simulated moving bed chromatography is a flow scheme that has been devised which maintains the process features of continuous countercurrent flow of fluid and solid without actual movement of the solid. The simulated moving bed technique has been described in R. A. Meyers, *Handbook of Petroleum Refining Processes*, pages 8–85 to 8–87, McGraw-Hill Book Company (1986). The technique has been applied commercially to a number of processes such as the separation of p-xylene from $C_8$ aromatic isomers, the separation of linear paraffins from branched-chain and cyclic hydrocarbons, and a process to separate fructose and glucose from mixtures thereof, to name just a few.

Simulated moving bed chromatography may be readily applied to the resolution of racemates simply by using a chiral adsorbent. See, e.g., M. Negawa and F. Shoji, *J. Chrom.*, 590, (1992), 113–7; M. J. Gattuso, B. McCullough, and J. W. Priegnitz presented at Chiral Europe '94 Symposium, Spring Innovations, Nice, France, Sep. 19–20, 1994.

A necessary feature of our invention is the adjustment of separation conditions to optimize the production of the desired enantiomer of high enantiomeric purity, i.e., optimize the formation of substantially pure desired enantiomer. By "substantially pure" is meant material of at least 95% enantiomeric purity, preferably at least 97% enantiomeric purity.

A specific embodiment involves the racemization of the undesired enantiomer obtained by SMB resolution of the racemate. Any racemization means proceeding at high yield and with good selectivity will suffice. Satisfaction of these requirements maximizes the utilization of racemic starting material while minimizing the overall process cost.

Referring to FIG. 1, the racemic tetralones are first reacted with a carbonyl protecting group, as is known in the art. This protecting group may optionally be chiral. The compound containing the protecting group may be, for example, an acetal, a ketal, an enol acetate, a mercaptan, and specific examples include, a ketal derived from a 1,2-glycol, a ketal derived from a 1,3-glycol, and a thioketal derived from a dithiol. These protected racemic tetralones are then resolved by simulated moving bed chromatography using a chiral adsorbent to afford the separated protected enantiomer of tetralones. The desired protected enantiomer of tetralones is then de-protected to the corresponding tetralones enantiomer, and is utilized in the synthesis of sertraline or sertraline analogs. The undesired protected tetralones enantiomer is racemized and recycled to the resolution stage.

An alternative preparation of chiral tetralones is shown in FIG. 2. In this case, the preparation of tetralones may begin with racemic alcohol derivatives in which the hydroxyl group is protected with a hydroxyl protecting group, which can be synthesized by methods known in the art. This protecting group may optionally be chiral. The compound containing the protecting group maybe, for example, an acetal, an ether, or an ester,; specific examples include, an acetal derived from a dihydropyran and an ether containing silicon. These protected racemic alcohols are then resolved by simulated moving bed chromatography using a chiral adsorbent to afford the separated protected alcohol enantiomers. The desired protected alcohol enantiomer is then de-protected to the corresponding alcohol, which is then oxidized to tetralones and utilized in the synthesis of sertraline or sertraline analogs. The undesired protected alcohol enantiomer is racemized and recycled to the resolution stage.

An alternative preparation of chiral tetralones is shown in FIG. 3. In this case, the preparation of tetralones may begin with racemic alcohol derivatives, which can be synthesized by methods known in the art. These racemic alcohols are then resolved using simulated moving bed chromatography using a chiral adsorbent to afford the separated alcohol enantiomers. The desired alcohol enantiomer is then oxidized to the corresponding chiral tetralone, which is utilized in the synthesis of sertraline or sertraline analogs. The undesired alcohol enantiomer is racemized and recycled to the resolution stage. Racemization may be effected in basic media by means well known in the art. Any racemization means will suffice so that the racemate is obtained in good yield, wvith high selectivity, and at a minimum cost.

What is claimed is:

1. In a process for preparation of compounds of formula III

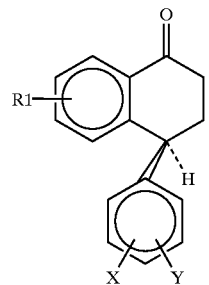

by selectively converting a carbonyl protected compound of formula V to III

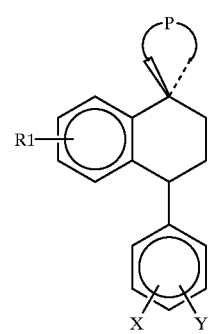

where R1 is selected from the group consisting of hydrogen, fluoro, chloro, bromo, trifluoromethyl, and alkoxy having from 1 to 3 carbon atoms, where X and Y are independently selected from the group consisting of hydrogen, fluoro, chloro, bromo, trifluoromethyl, cyano, and alkoxy having from 1 to 3 carbon atoms, with at least one of X or Y being other than hydrogen, and •~P~• is a carbonyl protecting group, the improvement comprising the selective preparation of III of at least 95% enantiomeric purity by:

a) resolving racemic V, in a resolution stage, by simulated moving bed chromatography using a chiral adsorbent to afford a first enantiomer of V in at least 95% enantiomeric purity and a second enantiomer of V;

b) selectively converting the first enantiomer of V to compound III; and c) racemizing the second enantiomer of V to racemic V and recycling the racemic V to the resolution stage.

2. The process of claim 1 wherein R1 is hydrogen.

3. The process of claim 1 wherein X is chlorine.

4. The process of claim 1 wherein Y is chlorine.

5. The process of claim 1 wherein V is a compound selected from the group consisting of an acetal, a ketal, an enol acetate, a mercaptal, and a thioketal.

6. The process of claim 1 wherein •~P~• contains at least one chiral center.

7. The process of claim 5 wherein V is a ketal derived from a 1,2-glycol or 1,3-glycol.

8. The process of claim 5 wherein V is a thioketal derived from a dithiol.

9. The process of claim 1 wherein in the first enantiomer of V is of at least 97% enantiomeric purity.

10. In a process for preparation of compounds of formula III

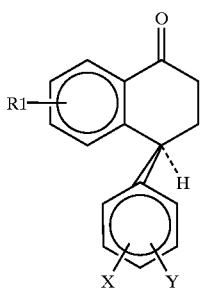

III by selectively converting a compound of formula VI or VII to III

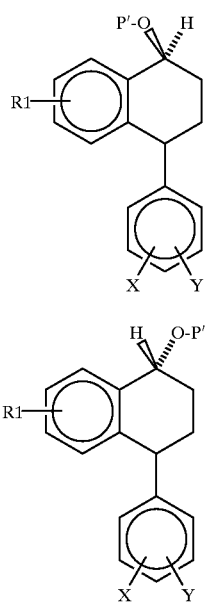

VI

VII where R1 is selected from the group consisting of hydrogen, fluoro, chloro, bromo, trifluoromethyl, and alkoxy having from 1 to 3 carbon atoms, where X and Y are independently selected from the group consisting of hydrogen, fluoro, chloro, bromo, trifluoromethyl, cyano, and alkoxy having from 1 to 3 carbon atoms, with at least one of X or Y being other than hydrogen, and P' is a hydroxyl protecting group, the improvement comprising the selective preparation of III of at least 95% enantiomeric purity by:
 a) resolving racemic VI or VII in a resolution stage by simulated moving bed chromatography using a chiral adsorbent to afford a first enantiomer of VI or VII in at least 95% enantiomeric purity and a second enantiomer of VI or VII;
 b) selectively converting the first enantiomer of VI or VII to compound III; and
 c) racemizing the second enantiomer of VI or VII to racemic VI or VII and recycling the racemic VI or VII to the resolution stage.

11. The process of claim 10 where R1 is hydrogen.
12. The process of claim 10 where X is chlorine.
13. The process of claim 10 where Y is chlorine.
14. The process of claim 10 where VI or VII is a compound selected from the group consisting of an acetal, an ether, and an ester.

15. The process of claim 10 where P' contains at least one chiral center.
16. The process of claim 14 where VI or VII is an acetal derived from a dihydropyran.
17. The process of claim 14 where VI or VII is an ether containing silicon.
18. The process of claim 10 wherein in the first enantiomer of VI or VII is of at least 97% enantiomeric purity.
19. In a process for preparation of compounds of formula III

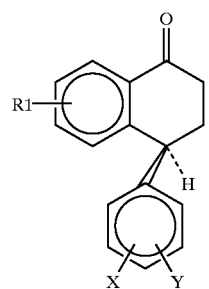

III by selectively converting a compound of formula VIII or IX to III

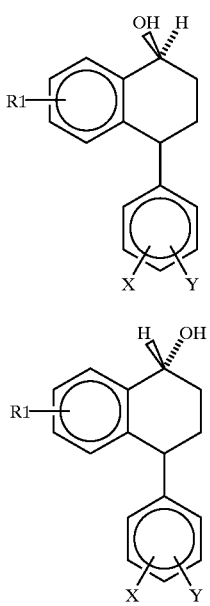

VIII

IX where R1 is selected from the group consisting of hydrogen, fluoro, chloro, bromo, trifluoromethyl, and alkoxy having from 1 to 3 carbon atoms, where X and Y are independently selected from the group consisting of hydrogen, fluoro, chloro, bromo, trifluoromethyl, cyano, and alkoxy having from 1 to 3 carbon atoms, with at least one of X or Y being other than hydrogen, the improvement comprising the selective preparation of III of at least 95% enantiomeric purity by:
 a) resolving racemic VIII or IX in a resolution stage by simulated moving bed chromatography using a chiral adsorbent to afford a first enantiomer of VIII or IX in at least 95% enantiomeric purity and a second enantiomer of VIII or IX;
 b) selectively converting the first enantiomer of VIII or IX to compound III; and c) racemizing the second enantiomer of VIII or IX to racemic VIII or IX and recycling the racemic VIII or IX to the resolution stage.

20. The process of claim 19 wherein R1 is hydrogen.
21. The process of claim 19 wherein X is chlorine.
22. The process of claim 19 wherein Y is chlorine.
23. The process of claim 19 wherein in the first enantiomer of VIII or IX is of at least 97% enantiomeric purity.

* * * * *